United States Patent
Katsuda et al.

(10) Patent No.: US 7,922,346 B2
(45) Date of Patent: Apr. 12, 2011

(54) MEDICAL LIGHTING APPARATUS AND MEDICAL IMAGING APPARATUS

(75) Inventors: Naoki Katsuda, Kyoto (JP); Shusuke Hashimoto, Kyoto (JP); Kazunari Matoba, Kyoto (JP); Shinichi Okawa, Kyoto (JP); Hiroaki Kusakabe, Kyoto (JP); Yuzo Nakayama, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 403 days.

(21) Appl. No.: 12/075,715

(22) Filed: Mar. 13, 2008

(65) Prior Publication Data

US 2008/0239697 A1    Oct. 2, 2008

(30) Foreign Application Priority Data

Mar. 16, 2007   (JP) .................................. 2007-068513
Mar. 16, 2007   (JP) .................................. 2007-068514

(51) Int. Cl.
*G03B 15/02*   (2006.01)
(52) U.S. Cl. .................. 362/5; 362/8; 362/16; 362/253; 362/572
(58) Field of Classification Search .................. 362/3, 5, 362/8, 11, 16, 227, 232, 253, 572–573
See application file for complete search history.

(56) References Cited

U.S. PATENT DOCUMENTS

| 4,608,622 A * | 8/1986 | Gonser ......................... 362/573 |
| 2007/0097703 A1 * | 5/2007 | Goldfain ......................... 362/572 |

FOREIGN PATENT DOCUMENTS

| JP | S57-134001 | 8/1982 |
| JP | 3084178 | 12/2001 |
| JP | 2004-355852 | 12/2004 |
| JP | 2005-158699 | 6/2005 |
| JP | 2005-222837 | 8/2005 |
| JP | 2005-317471 | 11/2005 |
| JP | 2006-288457 | 10/2006 |
| JP | 2007-052957 | 3/2007 |

* cited by examiner

*Primary Examiner* — Sandra L O Shea
*Assistant Examiner* — Meghan K Dunwiddie
(74) *Attorney, Agent, or Firm* — DLA Piper LLP (US)

(57) ABSTRACT

An object of the preset invention is to provide a medical lighting apparatus capable of illuminating an affected part with proper illuminance while assuring a work space for an operator near the affected part. A medical lighting apparatus for irradiating an affected part with light includes: a light source (a light emitting element); a light condenser (a collimate lens and a condenser lens) for condensing light emitted from the light source; an image forming unit (an image lens) for forming an image on the affected part from the light condensed by the light condenser; and an aperture portion provided between the light condenser and the image forming unit and regulating passage of the light condensed by the light condenser.

9 Claims, 11 Drawing Sheets

F I G. 1
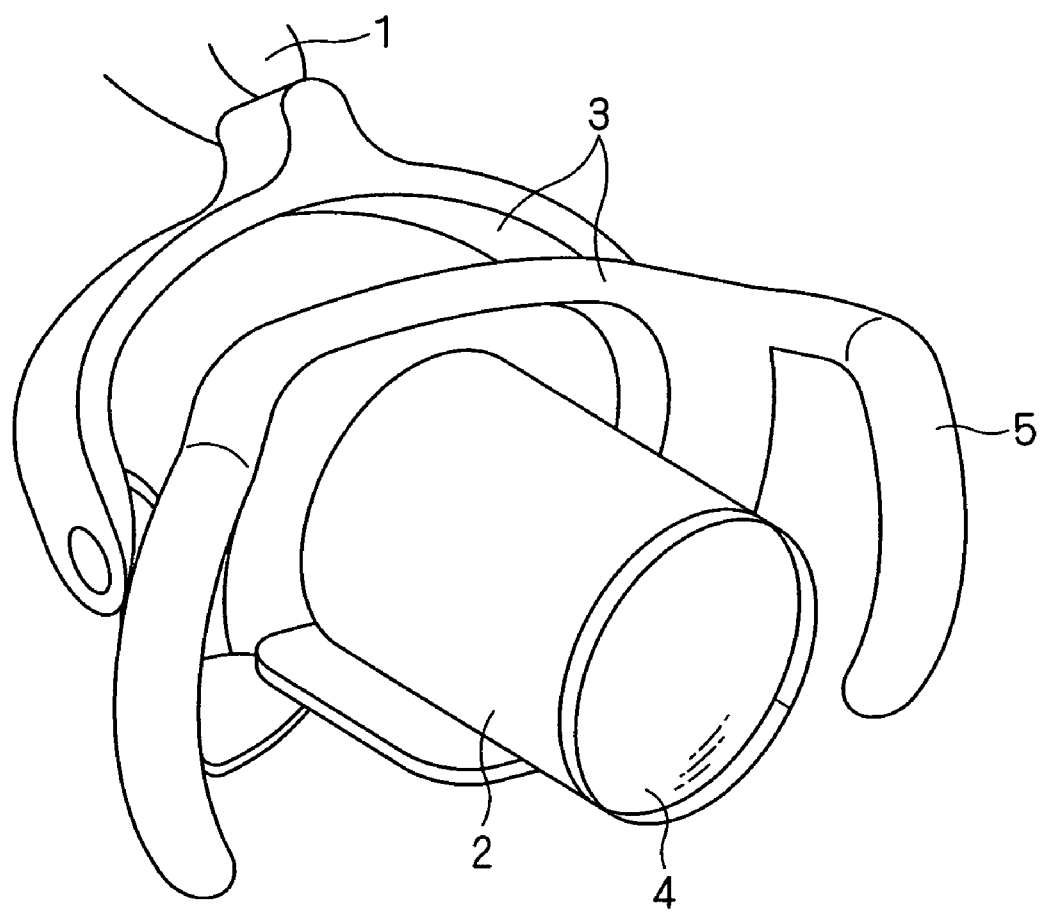

F I G. 5
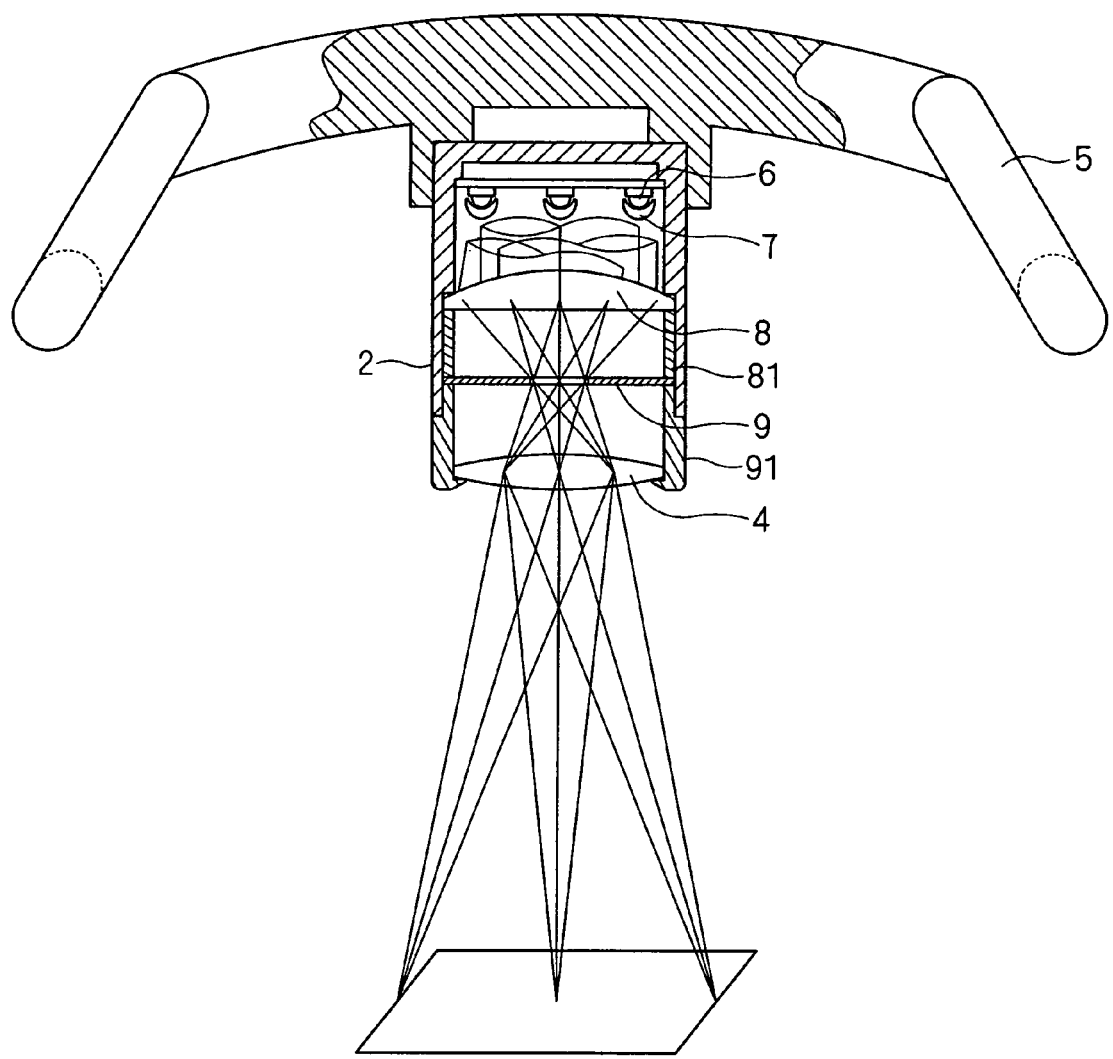

MEDICAL LIGHTING APPARATUS AND MEDICAL IMAGING APPARATUS

BACKGROUND OF THE INVENTION

1. Field of the Invention

The present invention relates to a technique for illuminating an affected part or capturing an image of an affected part while illuminating the affected part.

2. Description of the Background Art

At the time of treating an affected part, a medical lighting apparatus for illuminating the affected part with proper illuminance is required. In particular, a medical lighting apparatus for dental application is attached to a tip of a hanger arm mounted at a peripheral side portion of a treatment chair for dental application and swingable in a vertical or horizontal direction. To brightly illuminating the oral cavity of a patient on the treatment chair for dental application, the operator moves and turns on the medical lighting apparatus. A conventional medical lighting apparatus has a configuration that a halogen lamp is used as a light source and an affected part is irradiated with light reflected by a mirror plate. Recently, a medical lighting apparatus using an LED (Light Emitting Diode) as a light source as described in patent document 1 (Japanese Registered Utility Model No. 3,084,178) has been also developed.

Patent document 2 (Japanese Patent Application Laid-Open No. 2006-288457) discloses a lighting apparatus for dental application having illuminating means mounted on the side of a treatment chair for dental application and for illuminating the oral cavity of a patient on the treatment chair for dental application. In the lighting apparatus for dental application according to the patent document 2, light emitting means also has a function of emitting excitation light that makes a non-healthy part in the oval cavity emit fluorescence.

Patent document 3 (Japanese Patent Application Laid-Open No. 2004-237081) discloses an apparatus for capturing an image of an affected part inside an oral cavity and the like while illuminating the affected part.

The patent document 3 discloses a technique of disposing an LED (Light Emitting Diode) around image capturing means and, while illuminating an affected part by the LED, capturing an image of the illuminated affected part by the image capturing means.

SUMMARY OF THE INVENTION

It is, however, difficult to illuminate an affected part with proper illuminance by the conventional medical lighting apparatus using a halogen lamp as the light source and reflecting light by the mirror plate. Specifically, in the conventional medical lighting apparatus, because of the principle of irradiating an affected part with-reflection light from the mirror plate of light from the light source, only part of light generated omnidirectionally from the halogen lamp can be reflected. The irradiation efficiency therefore is very low, and it is necessary to use a halogen lamp with high brightness.

In the medical lighting apparatus of the patent document 1, in the case of using an LED simply in place of the halogen lamp, in order to obtain proper illuminance at an affected part, a plurality of LEDs have to be integrated at high density in a small space to achieve high brightness. It is therefore difficult to achieve it from the cost and technical viewpoints. The medical lighting apparatus according to the patent document 2 is the same as that of the conventional medical lighting apparatus with respect to the illuminating of an affected part. It is therefore difficult to illuminate an affected part with proper illuminance.

Therefore, a first object of the present invention is to provide a medical lighting apparatus capable of illuminating an affected part with proper illuminance while assuring a work space for an operator near a patient.

The patent document 3 relates to the configuration of irradiating an affected part with light from an LED. Consequently, when the LED is relatively far from the affected part, the affected part cannot be illuminated with proper illuminance.

For example, by integrating a number of LEDs at high density, relatively high illuminance can be obtained at the affected part. In this case, however, it is an important issue to make an irradiation range and an image capture range coincide with each other because there is limitation in mounting locations for the number of LEDs and the image capturing means.

Consequently, a second object of the present invention is to obtain proper illuminance even in an affected part apart from the light source and to make the irradiation range and the image capture range coincide with each other as much as possible.

To achieve the first object, according to a first aspect, a medical lighting apparatus for irradiating an affected part with light includes: a light source; a light condenser for condensing light emitted from the light source; an image forming unit for forming an image on the affected part from the light condensed by the light condenser; and an aperture portion provided between the light condenser and the image forming unit and regulating passage of the light condensed by the light condenser.

With the configuration, while assuring the space for performing a medical action and the like, an affected part can be illuminated with proper illuminance.

According to a second aspect, the medical lighting apparatus according to the first aspect further includes: a movable arm; and a frame for fixing the light source, the light condenser, the image forming unit, and the aperture portion to a tip of the movable arm.

With the configuration, the light source, the light condenser, and the aperture portion can be movably supported, the medical lighting apparatus can be properly moved, and a desired region can be efficiently irradiated with illumination light.

According to a third aspect, in the medical lighting apparatus according to the first or second aspect, the light source has, as a light emitting element, one of a light emitting diode, a halogen lamp, a krypton lamp, and a semiconductor laser.

With the configuration, various light emitting elements can be used for the light source.

According to a fourth aspect, in the medical lighting apparatus according to the first or second aspect, the light source has a plurality of light emitting elements, and the light condenser includes: collimate lenses each provided on a light emission face of each of the light emitting elements; and a condenser lens for condensing light from the collimate lenses.

With the configuration, while suppressing the number of light emitting elements, an affected part can be illuminated with proper illuminance, and the cost can be reduced.

According to a fifth aspect, in the medical lighting apparatus according to the fourth aspect, the light emitting element is a light emitting diode.

With the configuration, power consumption and the heat generation amount can be reduced.

According to a sixth aspect, in the medical lighting apparatus according to the first or second aspect, the light condenser includes: a reflection casing having an opening in an irradiation direction of the light source, reflecting light from the light source disposed internally, and outputting the light from the opening; and a condenser lens disposed in the opening and condensing the light outputted from the opening.

With the configuration, light from the light source can be efficiently condensed by the light condenser, and proper illuminance can be obtained by a smaller number of light emitting elements.

According to a seventh aspect, in the medical lighting apparatus according to the sixth aspect, the reflection casing is constructed by a hemi ellipsoid and a cylinder continued from an opening of the hemi ellipsoid, and the light source is disposed in an approximate focal point of the hemi ellipsoid.

With the configuration, since the light source is disposed in an approximate focal point of the hemi ellipsoid, light from the light source can be efficiently condensed.

According to an eighth aspect, in the medical lighting apparatus according to any of the first to seventh aspects, the aperture portion is disposed near a beam waist of the light condenser.

With the configuration, light from the light source is efficiently regulated to reduce the influence of ununiformity of the light source, so that uniform light can be obtained.

According to a ninth aspect, in the medical lighting apparatus according to any of the first to ninth aspects, the aperture portion has an approximately rectangular shaped opening.

With the configuration, an apparatus adapted to illuminate an affected part such as the oral cavity can be obtained.

To achieve the second object, according to a tenth aspect, a medical imaging apparatus for irradiating an affected part with light and capturing an image of the affected part includes: a light source; a light condenser for condensing light emitted from the light source; an image forming unit for forming an image on the affected part from the light condensed by the light condenser; an aperture portion provided between the light condenser and the image forming unit and regulating passage of the light condensed by the light condenser; and an imaging capturing unit for receiving reflected light from the affected part via the image forming unit and the aperture portion and capturing an image of the affected part.

Consequently, proper illuminance can be obtained even in an affected part remote from the light source. Since the image capturing unit for receiving reflected light from the affected part via the image forming unit and the aperture portion and capturing an image of the affected part is provided, the irradiation range and the image capture range can be made coincide with each other as much as possible. When an image of an affected part is not captured (the image capturing unit is not used as an image capturing apparatus), the unit can be used as a medical lighting apparatus.

According to an eleventh aspect, the medical imaging apparatus according to the first aspect further includes: a movable arm; and a frame for fixing the light source, the light condenser, the image forming unit, and the aperture portion to a tip of the movable arm.

With the configuration, the light source, the light condenser, the image forming unit, and the aperture portion can be movably supported. By properly moving the medical imaging apparatus, a desired region can be efficiently irradiated with illumination light, and a desired region to be imaged can be observed from the front.

According to a twelfth aspect, the medical imaging apparatus according to the tenth or eleventh aspect, the light source has, as a light emitting element, one of a light emitting diode, a halogen lamp, a krypton lamp, and a semiconductor laser.

With the configuration, various light emitting elements can be used for the light source.

According to a thirteenth aspect, in the medical imaging apparatus according to any of the tenth to twelfth aspects, the light source has a plurality of light emitting elements, and the light condenser includes: collimate lenses each provided on a light emission face of each of the light emitting elements; and a condenser lens formed in an approximately annular shape with a hole in an approximate center portion, and for condensing light from the collimate lenses, and the image capturing unit receives reflected light from the affected part via the hole in the condenser lens.

With the configuration, light from each of the light emitting elements can be efficiently condensed. Since the image capturing unit receives reflected light from the affected part via the hole in the condenser lens, the center of the range of irradiation from the light source and the center of the image capture range can be made almost coincide with each other. Further, at the time of capturing an image, the influence of the light condenser can be eliminated.

According to a fourteenth aspect, in the medical imaging apparatus according to the thirteenth aspect, the plurality of light emitting elements are disposed in an approximately annular shape.

With the configuration, an affected part can be brightly irradiated with light from the plurality of light emitting elements disposed annularly.

According to a fifteenth aspect, in the medical imaging apparatus according to the thirteenth or fourteenth aspect, the light emitting element is a light emitting diode.

With the configuration, power consumption and the heat generation amount can be reduced.

According to a sixteenth aspect, in the medical imaging apparatus according to any of the tenth to fifteenth aspects, the aperture portion is disposed near a beam waist of the light condenser.

With the configuration, light from the light source is efficiently regulated to reduce the influence of ununiformity of the light source, so that uniform light can be obtained.

According to a seventeenth aspect, in the medical imaging apparatus according to any of the tenth to sixteenth aspects, the aperture portion has an approximately rectangular shaped opening.

With the configuration, an apparatus adapted to illuminate an affected part such as the oral cavity can be obtained.

According to an eighteenth aspect, in the medical imaging apparatus according to any of the tenth to seventeenth aspects, the image capturing unit is disposed on a central axis of the light condenser and the image forming unit and has a zoom mechanism.

With the configuration, while maintaining the center of the irradiation range constant, the image capture range can be e.g. reduced/enlarged.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic diagram of a medical lighting apparatus according to a first embodiment;

FIG. 5 is a schematic diagram for explaining optical characteristics of the medical lighting apparatus according to the first embodiment;

DESCRIPTION OF THE PREFERRED EMBODIMENTS

First Embodiment

Outline of Apparatus

Figure 2:
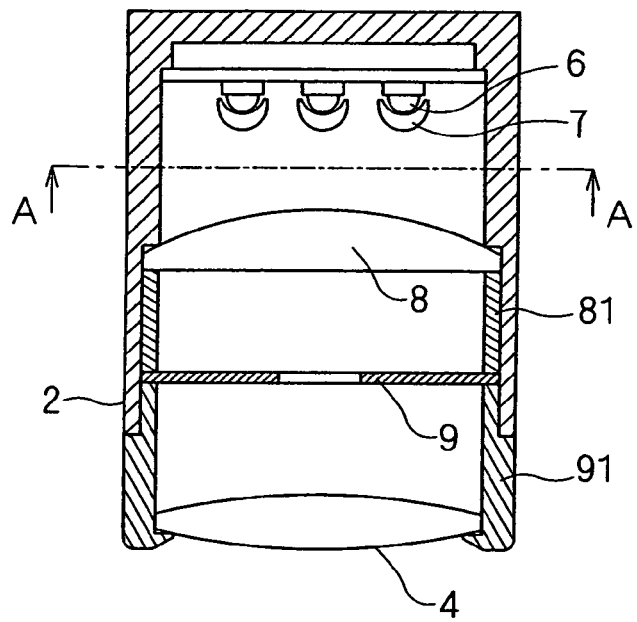
FIG. 2 is a cross sectional view of the medical lighting apparatus according to the first embodiment.

FIG. 1 is a schematic diagram of a medical lighting apparatus of a first embodiment. The medical lighting apparatus shown in FIG. 1 is obtained by providing a movable arm 1 with a frame 3 for fixing a cylinder body 2 that holds an optical part as a light source. FIG. 1 shows a state where an imaging lens 4 as one of the optical parts is held in the cylinder body 2. A handle 5 is attached to the frame 3 so that an operator of the medical lighting apparatus can easily move it.

For example, in the case where the medical lighting apparatus shown in FIG. 1 is used in dental application, the medical lighting apparatus is mounted on the side of a dental treatment chair (not shown) and used for irradiating the oral cavity (affected part) of a patient on the dental treatment chair. In the following, the medical lighting apparatus mainly for dental application will be described. The medical lighting apparatus according to the present invention is not limited in dental application but can be also applied to other medial fields such as otolaryngologic application.

Optical Configuration of Apparatus

Figure 3:
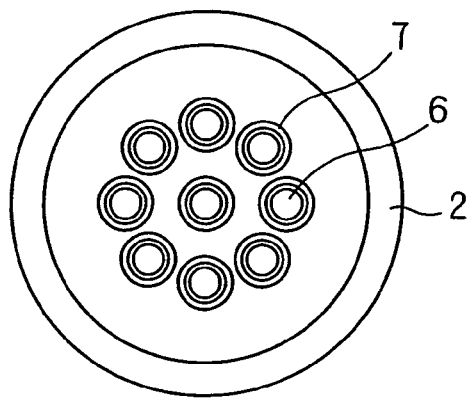
FIG. 3 is a schematic diagram of a light source of the medical lighting apparatus according to the first embodiment.

The optical configuration of the medical lighting apparatus according to the present embodiment will now be described. FIG. 2 is a cross sectional view of the cylindrical body 2 of the present embodiment. A plurality of light emitting elements 6 as light sources are provided at one end of the cylindrical body 2 shown in FIG. 2. As shown in FIG. 3 as a cross sectional view at A-A plane of FIG. 2, eight light emitting elements 6 are disposed annularly, and one light emitting element 6 is disposed at the center. LEDs (Light Emitting Diodes) are used as the light emitting elements 6. The present invention is not limited thereto, and halogen bulbs, krypton bulbs, semiconductor lasers, and the like may be used as the light emitting elements 6. The disposition and the number of light emitting elements 6 are not limited to those of FIG. 3 but it is sufficient to suitably select disposition and the number of light emitting elements 6 by which illuminance necessary in an affected part can be obtained.

In the cylindrical body 2 shown in FIG. 2, a collimate lens 7 is provided at the light emitting face of each of the light emitting elements 6. The collimate lens 7 may be physically separated from each of the light emitting elements 6 as shown in FIG. 2 or formed integrally with the light emitting element 6. The cylindrical body 2 shown in FIG. 2 is provided with a condenser lens 8 such as a convex lens or Fresnel lens in a position apart from the collimate lens 7 by a predetermined distance. The condenser lens 8 shown in FIG. 2 is fixed with a condenser lens retainer 81 on the inner side of the cylindrical body 2. Although a planoconvex lens which is projected toward the light emitting element 6 side is used as the condenser lens, the present invention is not limited thereto. As long as desired condensed light can be obtained, a biconvex lens may be used. Although the condenser lens 8 shown in FIG. 2 is constructed as a single lens, the present invention is not limited thereto. A plurality of lenses may be combined. The collimate lens 7 and the condenser lens 8 construct a condenser unit in the present embodiment. In the case of using the light emitting element 6 generating parallel rays (for example, an LED in which a collimate lens is molded on the light emitting face), only the condenser lens 8 constructs the condenser unit.

The imaging lens 4 as an image forming unit for forming an image by light condensed by the condenser unit on an affected part is provided at the other end of the cylindrical body 2 shown in FIG. 2. Although the imaging lens 4 shown in FIG. 2 is a biconvex lens, the present invention is not limited thereto but the imaging lens 4 may be a planoconvex lens. Although the imaging lens 4 shown in FIG. 2 is constructed as a single lens, the present invention is not limited thereto. A plurality of lenses may be combined.

Figure 4:
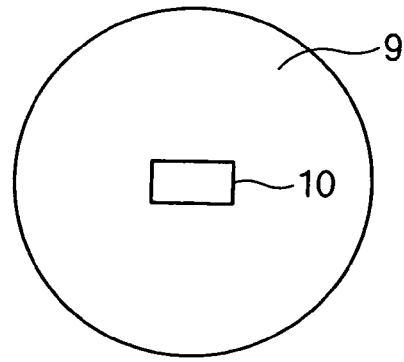
FIG. 4 is a schematic diagram of an aperture portion of the medical lighting apparatus according to the first embodiment.

As shown in FIG. 2, an aperture portion 9 is provided between the imaging lens 4 and the condenser lens 8 in the cylindrical body 2 and fixed by the condenser lens retainer 81 and an aperture retainer 91. A rectangular opening 10 is formed in the aperture portion 9 as shown in FIG. 4. The shape of the opening 10 is determined in consideration of the shape in which an affected part is illuminated and the like, and is not always limited to the rectangular shape. The illumination range of the medical lighting apparatus for dental application is set to a range (about 80×150 mm) slightly wider than the oral cavity of a patient. The aperture portion 9 can be obtained by forming the opening 10 in a metal plate. The aperture portion 9 may be provided with a mechanical mechanism so that the shape of the opening 10 can be varied or a liquid crystal aperture portion can be also used. The aperture portion 9 itself may be replaced with any of apertures having openings 10 in various shapes.

In the present embodiment, the positions of the imaging lens 4 and the aperture portion 9 can be moved. Although not shown in FIG. 2, the cylindrical body 2 may be provided with a part for moving the imaging lens 4 and the aperture portion 9. The distance between the imaging lens 4 and the affected part is about 400 to 900 mm to sufficiently assure a work space for the operator to treat the affected part.

Optical Characteristics of Apparatus

The optical characteristics of the apparatus will now be described with reference to the schematic diagram of the medical lighting apparatus according to the present embodiment shown in FIG. 5. First, light emitted from the light emitting elements 6 provided at one end of the cylindrical body 2 is converted to approximately parallel rays by the collimate lens 7. In the medical lighting apparatus according to the present embodiment, nine LEDs are provided as the light emitting elements 6 as shown in FIG. 3, and light from the light emitting elements 6 is converted to approximately parallel rays by the collimate lenses 7. Generally, when the LEDs are arranged at high density, seven is the preferable.

The light from the light emitting elements 6 that has become approximately parallel rays is condensed to a predetermined position by the condenser lens 8 as shown in FIG. 5. That is, in the medical lighting apparatus according to the present embodiment, to condense light from the light emitting elements 6 as light sources to a predetermined position, approximately parallel rays are once generated by each of the collimate lenses 7. The parallel rays are condensed to a common focal point by the single condenser lens 8.

The light condensed by the condenser lens 8 is blocked except for light passing through the opening 10 in the aperture portion 9. Desirably, the aperture portion 9 is positioned near a beam waist of the condenser lens 8 for the reason that the light of the light source consisting of the plurality of light emitting elements 6 is efficiently controlled and the light is made uniform by reducing the influence of ununiformity. The beam waist corresponds to a position where the diameter of the irradiation light condensed by the condenser lens is the smallest. When the irradiation light is not always condensed into a single point, the meaning of the beam waist is almost the same as a focus position.

The opening 10 in the aperture portion 9 has a rectangular shape as shown in FIG. 4, and light passed through the aperture portion 9 passes through the imaging lens 4 and falls on the affected part. That is, in the medical lighting apparatus according to the present embodiment, an image of light in the rectangular shape formed in the aperture portion 9 is formed on the affected part by the imaging lens 4. In the case of using the medical lighting apparatus according to the present embodiment for dental application, the size of the opening 10 in the aperture portion 9, the optical characteristics of the imaging lens 4, and the distance between the aperture portion 9 and the imaging lens 4 are determined so that the range of the affected part to be illuminated becomes about 80 mm×150 mm and the distance from the imaging lens 4 to the affected part becomes about 400 to 900 mm.

As described above, in the medical lighting apparatus according to the present embodiment, the light emitted from the light emitting elements 6 as the light source is condensed by the condenser unit (the collimate lens 7 and the condenser lens 8), and an image is formed on the affected part by the image forming unit (the imaging lens 4) via the aperture portion 9. Consequently, the light can be efficiently collected from the light emitting elements 6 and irradiate the affected part. That is, in the medical lighting apparatus according to the present embodiment, while suppressing the number of light emitting elements, an affected part can be illuminated with proper illuminance, so that the cost can be reduced. Further, since the medical lighting apparatus according to the present embodiment uses the optical configuration of the imaging system, while assuring the work space for the operator near an affected part, the affected part, preferably only the affected part, can be illuminated with proper illuminance.

The sectional shape of the cylindrical body 2 of the medical lighting apparatus according to the present embodiment has been described as a circular shape. The present invention is not limited thereto, and the sectional shape of the cylindrical body 2 may be another shape such as a rectangular shape.

Application Examples

In the case of using LEDs as the light emitting elements 6 as an application example of the medical lighting apparatus according to the present embodiment, an LED of white color and an LED having a wavelength of 400±20 nm are incorporated and turned on while being switched. It is known that when the oral cavity is irradiated with light having a wavelength of 400±20 nm in a dental diagnosis, a part where dental calculi or dental plaque is attached emits red fluorescence. It is also known that when the oral cavity is irradiated with light having a wavelength of 400±20 nm, an image useful for diagnosing a carious part can be obtained, so that detection of a lesion part is facilitated. Consequently, by further incorporating the LED having a wavelength of 400±20 nm as an application example of the medical lighting apparatus according to the present embodiment, in addition to the function of irradiating an affected part, dental diagnosis can be performed with the light having a wavelength of 400±20 nm.

In the case of using LEDs as the light emitting elements 6 as another application example of the medical lighting apparatus according to the present embodiment, an LED of white color and an LED having a wavelength of 470±20 nm are incorporated and turned on while being switched. In the dental treatment, light having a wavelength of 470±20 nm is used to photopolymerize the resin of an affected part. Consequently, by further incorporating the LED having a wavelength of 470±20 nm as another application example of the medical lighting apparatus according to the present embodiment, in addition to the function of irradiating an affected part, dental treatment such as the polymerization of resin can be performed with the light having a wavelength of 470±20 nm.

In the case of using LEDs as the light emitting elements 6 as another application example of the medical lighting apparatus according to the present embodiment, an LED of white color and an LED having a wavelength of 405±20 nm are incorporated and turned on while being switched or simultaneously turned on. In the dental field, light having a wavelength of 405±20 nm is used also for bleaching teeth. Consequently, by further incorporating the LED having a wavelength of 405±20 nm as another application example of the medical lighting apparatus according to the present embodiment, in addition to the function of irradiating an affected part, teeth can be bleached with the light having a wavelength of 405±20 nm. The light having a wavelength of 405±20 nm has an action of exciting fluorescence from carious or dental calculi and dental plaque, so that it can be also used for diagnosing the lesion.

Second Embodiment

Outline of Apparatus

The configuration of a medical lighting apparatus according to a second embodiment is the same as that of the first embodiment as shown in the schematic diagram of FIG. 1 except for the optical configuration of the cylindrical body 2. Therefore, the detailed description will not be repeated.

Optical Configuration of Apparatus

Figure 6:
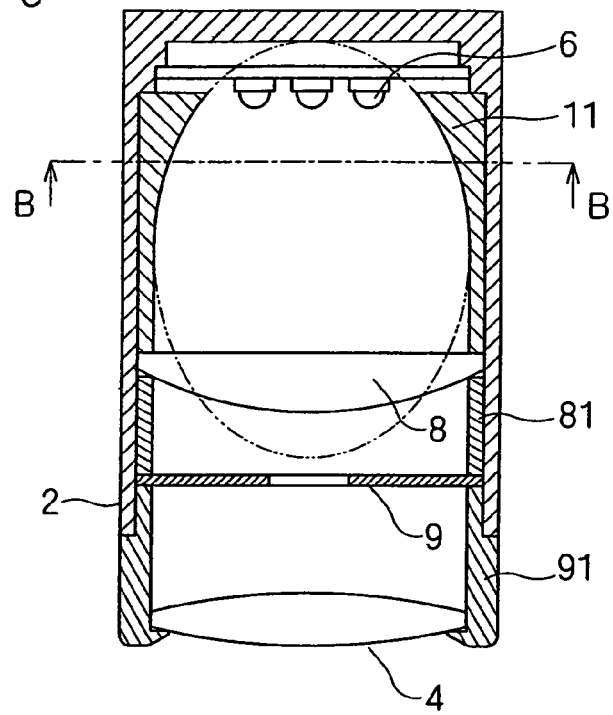
FIG. 6 is a cross sectional view of a medical lighting apparatus according to a second embodiment.
Figure 7:
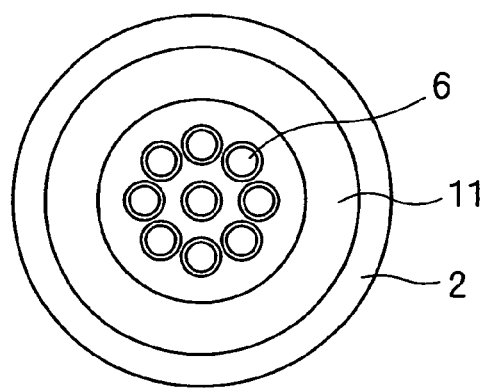
FIG. 7 is a schematic diagram of a light source of the medical lighting apparatus according to the second embodiment.

The optical configuration of the medical lighting apparatus according to the second embodiment will now be described. FIG. 6 is a cross sectional view of the cylindrical body 2 according to the present embodiment. A plurality of light emitting elements 6 as light sources are provided at one end of the cylindrical body 2 shown in FIG. 6. As shown in FIG. 7 as the cross sectional view on B-B plane of FIG. 6, eight light emitting elements 6 are disposed annularly, and one light emitting element 6 is disposed at the center. Although LEDs are used as the light emitting elements 6, the present invention is not limited thereto. Halogen bulbs, krypton bulbs, semiconductor lasers, and the like may be used as the light emitting elements 6. The disposition and the number of light emitting elements 6 are not limited to those of FIG. 7 but it is sufficient to suitably select disposition and the number of light emitting elements 6 by which illuminance necessary in an affected part can be obtained.

Figure 8:
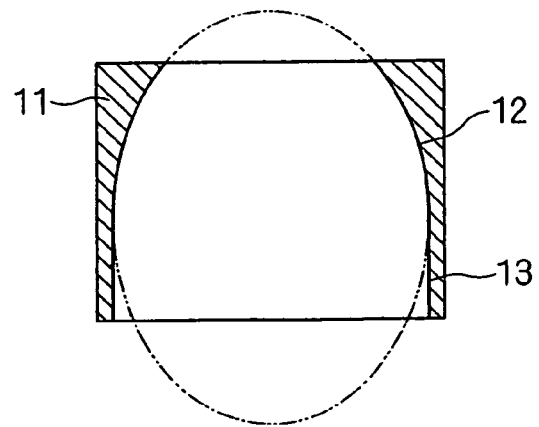
FIG. 8 is a schematic diagram of a reflection casing of the medical lighting apparatus according to the second embodiment.

In the cylindrical body 2 shown in FIG. 6, in place of the collimate lens 7 shown in FIG. 2 of the first embodiment, a reflection casing 11 is provided. The reflection casing 11 has a shape in which the part of an aspherical mirror 12 having e.g. a paraboloidal shape and the part of a cylindrical mirror 13 are continuous as shown in FIG. 8 and has an opening in the irradiation direction of the light emitting elements 6. A more desirable shape of the reflection casing 11 is one in which the aspherical mirror 12 has a hemi ellipsoidal shape and the cylindrical mirror 13 has a cylinder continued from the opening of the hemi ellipsoidal shape. In the case where the reflection casing 11 is constructed by a hemi ellipsoidal shape and a cylinder, the light emitting elements 6 are disposed in an approximate focal point of the hemi-ellipsoidal cylindrical mirror 13. The shape of the reflection casing 11 according to the present invention need not necessarily have the part of the cylindrical mirror 13. It is sufficient that the reflection casing 11 has the opening in the irradiation direction of the light emitting elements 6 (light source), reflects light from the light emitting elements 6 (light source) disposed inside, and emits the light from the opening.

Further, in the cylindrical body 2 shown in FIG. 6, the condenser lens 8 such as a convex lens or a Fresnel lens is provided at the opening of the reflection casing 11. Although the condenser lens 8 shown in FIG. 6 is a planoconvex lens which is convex on the light emitting element 6 side, the present invention is not limited thereto. As long as desired condensed light can be obtained, a biconvex lens may be used. Although the condenser lens 8 shown in FIG. 6 is constructed as a single lens, the present invention is not limited thereto. A plurality of lenses may be combined. The reflection casing 11 and the condenser lens 8 construct a condenser unit in the present embodiment.

In a manner similar to the first embodiment, the imaging lens 4 as an image forming unit for forming an image by light condensed by the condenser unit on an affected part is provided at the other end of the cylindrical body 2 shown in FIG. 6. Although the imaging lens 4 shown in FIG. 6 is a biconvex lens, the present invention is not limited thereto but the imaging lens 4 may be a planoconvex lens. Although the imaging lens 4 shown in FIG. 6 is constructed as a single lens, the present invention is not limited thereto. A plurality of lenses may be combined.

In a manner similar to the first embodiment, as shown in FIG. 6, the aperture portion 9 is provided between the imaging lens 4 and the condenser lens 8. The rectangular opening 10 is formed in the aperture portion 9 as shown in FIG. 4 of the first embodiment. The shape of the opening 10 is determined in consideration of the shape in which an affected part is illuminated and the like, and is not always limited to the rectangular shape. The illumination range of the medical lighting apparatus for dental application is set to a range (about 80×150 mm) slightly wider than the oral cavity as the affected part. The aperture portion 9 can be obtained by forming the opening 10 in a metal plate. The aperture portion 9 may be provided with a mechanical mechanism so that the shape of the opening 10 can be varied or a liquid crystal aperture portion can be also used.

Also in the second embodiment, in a manner similar to the first embodiment, the positions of the imaging lens 4 and the aperture portion 9 can be moved. Although not shown in FIG. 6, the cylindrical body 2 may be provided with a unit for moving the imaging lens 4 and the aperture portion 9. The distance between the imaging lens 4 and the affected part is about 400 to 900 mm to sufficiently assure a work space for the operator to treat the affected part.

Optical Characteristics of Apparatus

The optical characteristics of the apparatus will now be described with reference to the schematic diagram of the medical lighting apparatus according to the present embodiment shown in FIG. 9. First, light emitted from the light emitting elements 6 provided at one end of the cylindrical body 2 is reflected by the reflection casing 11. In the medical lighting apparatus according to the present embodiment, nine light emitting elements 6 as LEDs shown in FIG. 7 are provided in an approximate focal point of the reflection casing 11 (cylindrical mirror 13) having a hemi ellipsoidal shape. Consequently, the light emitted from the light emitting elements 6 is reflected by the reflection casing 11 and outputted from a position near the focal point in the case where the reflection casing 11 (cylindrical mirror 13) has an oval sphere shape.

Figure 9:
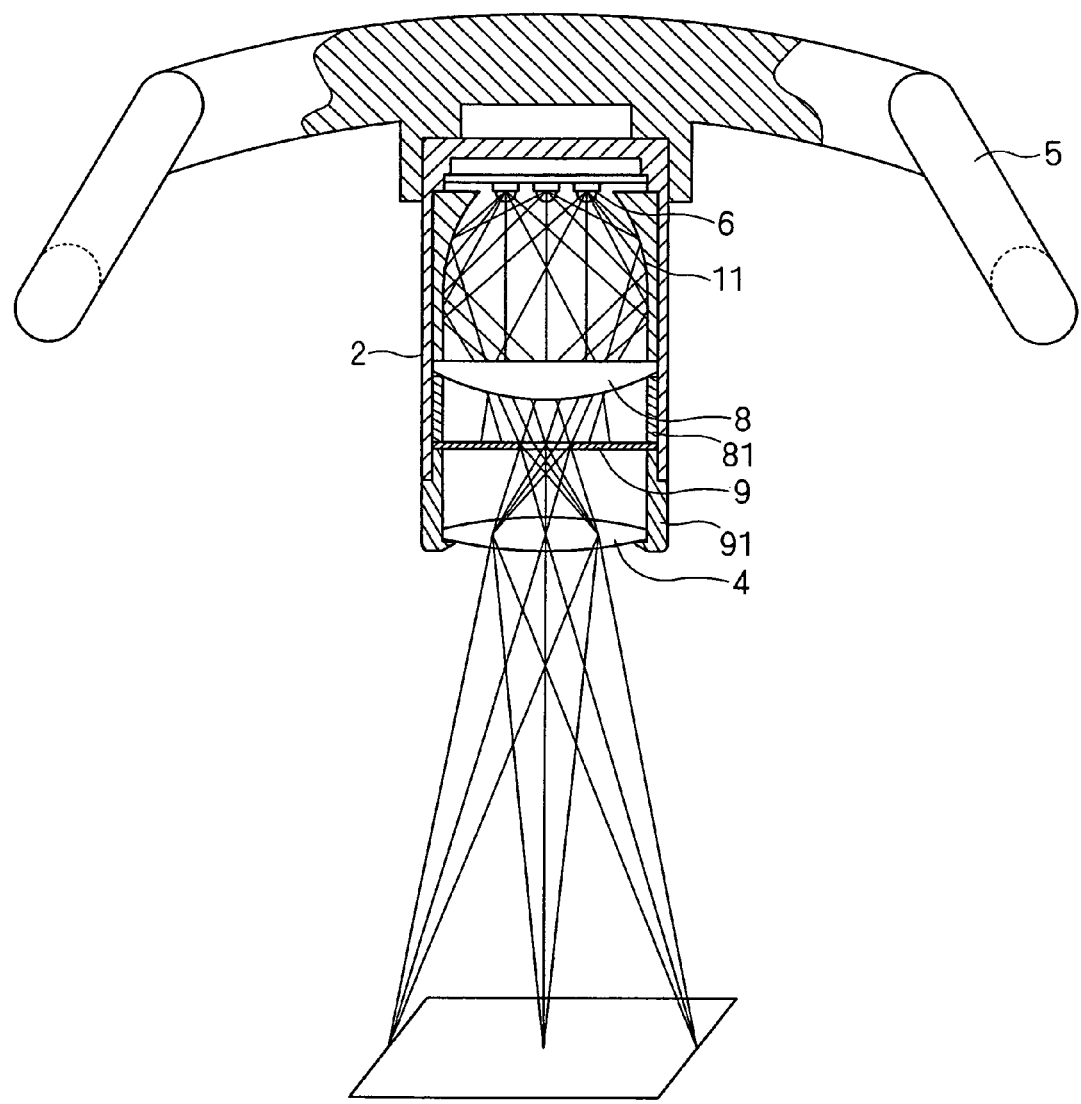
FIG. 9 is a schematic diagram for explaining optical characteristic of the medical lighting apparatus according to the second embodiment.

The condenser lens 8 shown in FIG. 9 is provided in a position near the focal point in the case where the reflection casing 11 (the cylindrical mirror 13) has an oval sphere shape, and condenses light from the light emitting elements 6 to a predetermined position. That is, in the medical lighting apparatus according to the present embodiment, in place of the collimate lens 7 and the condenser lens 8, the light emitted from the light source is condensed by the reflection casing 11 and the condenser lens 8.

The light condensed by the condenser lens 8 is then blocked except for light passing through the opening 10 in the aperture portion 9. Desirably, the aperture portion 9 is positioned near a beam waist condensed by the condenser lens 8 in order to make the light uniform by reducing the influence of ununiformity of the light source constructed with the plurality of light emitting elements 6.

The opening 10 in the aperture portion 9 has a rectangular shape as shown in FIG. 4 of the first embodiment, and the light passed through the aperture portion 9 is applied to the affected part via the imaging lens 4. That is, also in the medical lighting apparatus according to the present embodiment, since the optical configuration subsequent to the condenser lens 8 is the same as that in the first embodiment, an image of light in the rectangular shape formed in the aperture portion 9 is formed on the affected part by the imaging lens 4. In the case of using the medical lighting apparatus according to the present embodiment for dental application, the size of the opening 10 in the aperture portion 9, the optical characteristics of the imaging lens 4, and the distance between the aperture portion 9 and the imaging lens 4 are determined so that the range of the affected part to be illuminated becomes about 80 mm×150 mm and the distance from the imaging lens 4 to the affected part becomes about 400 to 900 mm.

As described above, in the medical lighting apparatus according to the present embodiment, light emitted from the light emitting elements 6 as the light source is condensed by the condenser unit (the reflection casing 11 and the condenser lens 8), and an image is formed on the affected part by the image forming unit (the imaging lens 4) via the aperture portion 9. Consequently, the light can be efficiently collected from the light emitting elements 6 and irradiate the affected part. That is, in the medical lighting apparatus according to the present embodiment, while suppressing the number of light emitting elements, an affected part can be illuminated with proper illuminance, so that the cost can be reduced. Further, since the medical lighting apparatus according to the present embodiment uses the optical configuration of the imaging system, while assuring a work space for the operator near an affected part, the affected part can be illuminated with proper illuminance.

The sectional shape of the cylindrical body 2 of the medical lighting apparatus according to the present embodiment has been described as a circular shape. The present invention is not limited thereto. The sectional shape of the cylindrical body 2 may be another shape such as a rectangular shape. In the case where the sectional shape of the cylindrical body 2 is a rectangular shape, the aspherical mirrors 12 may be formed on only a set of opposite faces or on all of the faces.

Application Examples

The application example of the first embodiment can be also employed for the medical lighting apparatus according to the second embodiment. The configuration of an application example of the medical lighting apparatus according to the second embodiment is the same as that of the application example of the first embodiment, so that the detailed description will not be repeated.

Third Embodiment

A medical imaging apparatus according to a third embodiment will be described hereinbelow.

Figure 10:
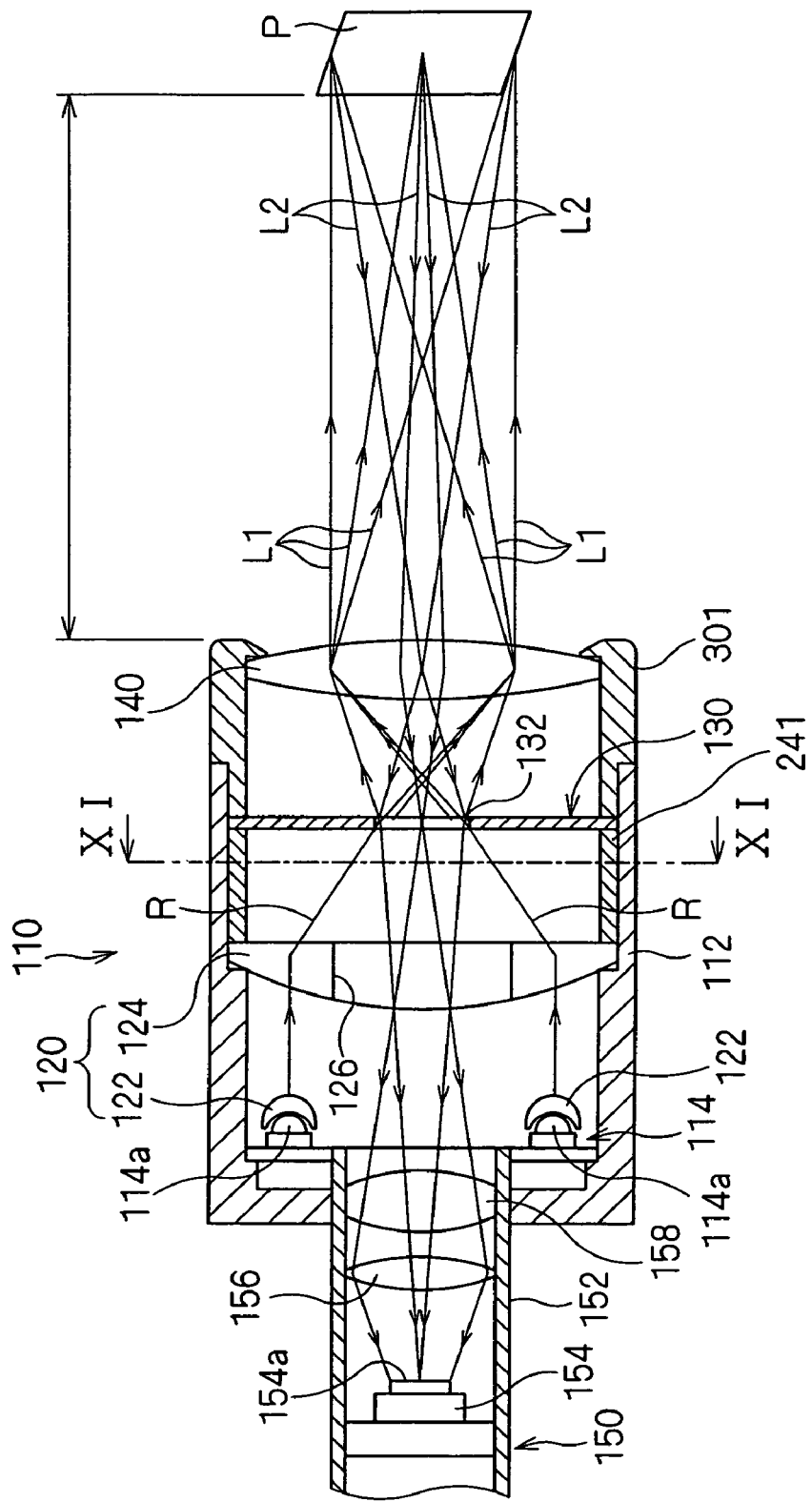
FIG. 10 is a schematic cross sectional view showing a medical imaging apparatus according to a third embodiment.
Figure 11:
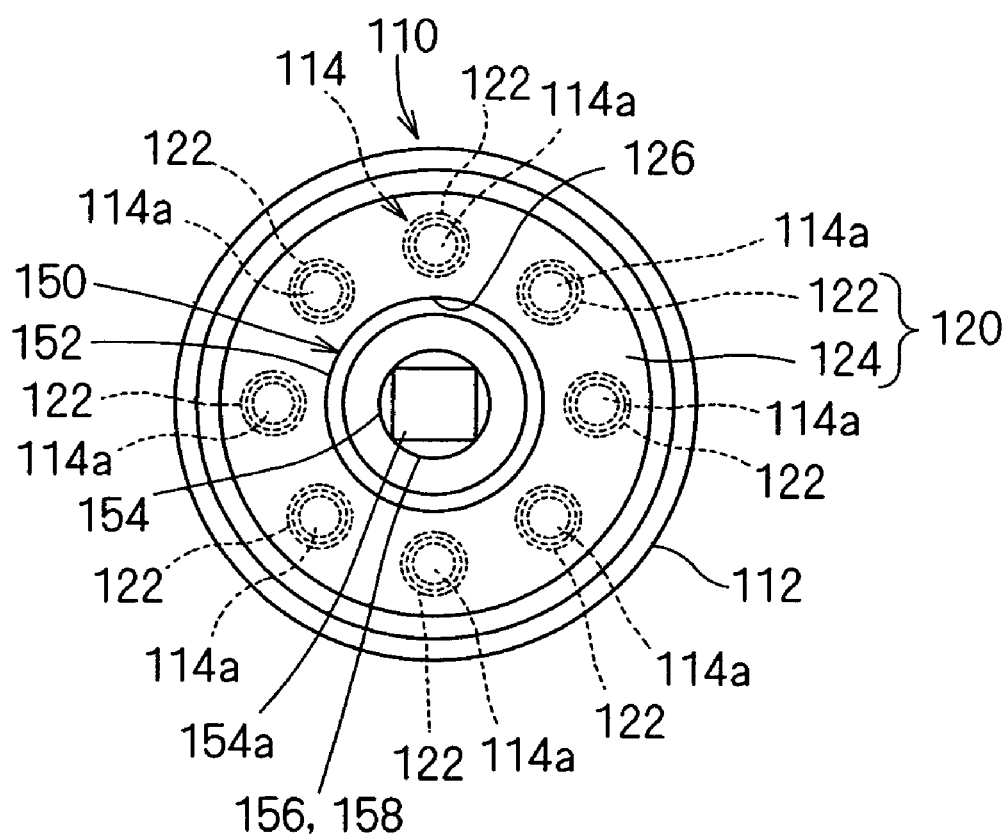
FIG. 11 is a cross sectional view taken along line XI-XI of FIG. 10;.

FIG. 10 is a schematic cross sectional view of the medical imaging apparatus. FIG. 11 is a cross sectional view taken along line XI-XI of FIG. 10.

A medical imaging apparatus 110 is used in, for example, dental application and used for capturing an image of the oral cavity (affected part) P of a patient while emitting light to the affected part P.

Basic Configuration of Medical Imaging Apparatus

The medical imaging apparatus 110 has a light source 114, a light condenser 120, an aperture portion 130, an imaging forming unit 140, and an image capturing unit 150.

The light source 114, the light condenser 120, the aperture portion 130, and the image forming unit 140 are disposed in this order along the axial direction of a cylindrical body 112 in the cylindrical body 112. The image capturing unit 150 is disposed at one end of the cylindrical body 112. The central axis of the cylindrical body 112 is a reference axis also serving as the central axis of the light condenser 120, the image forming unit 140, the image capturing unit 150, and the like. The cylindrical body 112 may have a cylindrical shape or an angular cylindrical shape.

The light source 114 emits light and has a plurality of light emitting elements 114a.

Six light emitting elements 114a are disposed in an annular shape centered at the central axis of the cylindrical body 112 (refer to FIG. 11). LEDs (Light Emitting Diodes) are used as the light emitting elements 114a. The light emitting elements 114a are not limited to LEDs but halogen bulbs, krypton bulbs, semiconductor lasers, and the like may be used as the light emitting elements 114a. The disposition and the number of light emitting elements 114a are not limited to those of the example shown in FIG. 11 but it is sufficient to suitably select disposition and the number of light emitting elements 114a by which illuminance necessary in an affected part P can be obtained. For example, two light emitting elements 114a may be provided in the horizontal direction or vertical direction while sandwiching the central axis of the cylindrical body 112. The light emitting elements 114a may be disposed in a double or more annular shape centered at the central axis of the cylindrical body 112. Specifically, it is sufficient to provide the light emitting elements 114a in positions where the reflected light from the affected part P is allowed to enter an imaging device 154. That is, it is sufficient that the light emitting elements 114a are provided around the optical path of the reflected light.

The light condenser 120 is an optical element for condensing light emitted from the light source 114. The light condenser 120 has collimate lenses 122 and condenser lenses 124 provided for the light emitting elements 114a.

Each of the collimate lenses 122 is disposed on the light emission face side of each of the light emitting elements 114a. The collimate lens 122 may be physically separated from the light emitting element 114a or formed integrally with the light emitting element 114a. In the case of using the light emitting element 114a generating approximately parallel rays (for example, an LED in which a collimate lens is molded to the light emission face), the collimate lens 122 may not be used.

The condenser lens 124 is an optical element disposed in a position apart from the collimate lens 122 by a predetermined distance along the axial direction of the cylindrical body by a condenser lens hold 241 in the cylindrical body 112 and for condensing light from each of the collimate lenses 122. As such a condenser lens 124, a convex lens, a Fresnel lens, or the like is used. In FIG. 10, the condenser lens 124 is shown as a planoconvex lens. As long as desired condensed light can be obtained, a biconvex lens or the like may be used. The condenser lens 124 may be constructed by combining a plurality of lenses.

A hole 126 is formed in an approximate center part of the condenser lens 124. The whole shape of the condenser lens 124 is approximately an annular shape. The hole 126 is formed in a position off the optical path along which the reflected light from the affected part P enters the image capturing unit 150. As long as the optical path is not disturbed, the hole 126 is not limited to an approximately circular shape but may be an approximately oval shape or an approximately rectangle shape. The reflected light from the affected part P enters the image capturing unit 150 without being e.g. refracted by the condenser lens 124.

The image forming unit 140 is an optical element for forming an image by light condensed by the light condenser 120 on the affected part P. The image forming unit 140 is a biconvex lens and provided at the other end of the cylindrical body 112. The image forming unit 140 may be a Fresnel lens or a planoconvex lens. The image forming unit 140 may be constructed by combining a plurality of lenses.

The aperture portion 130 is provided between the image forming unit 140 and the condenser lens 124 in the cylindrical body 112 and is fixed by the condenser lens hold 241 and an aperture hold 301. The aperture portion 130 is a plate-shaped member and a rectangular-shaped opening 132 is formed in an approximate center portion of the aperture portion 130. The aperture portion 130 has a role of regulating passage of light condensed by the light condenser 120. The shape of the opening 132 is determined in consideration of the range of an affected part P to be illuminated and the like, and is not always limited to the rectangular shape. Preferably, the illumination range of the medical imaging apparatus for dental application is set to a range (e.g., about 80 mm×150 mm) slightly wider than the oral cavity of a patient, so that the opening 132 is formed in a rectangular shape according to the range. The aperture portion 130 can be obtained by forming the opening 132 in a plate member such as a metal plate. The aperture portion 130 may be provided with a mechanical mechanism so that the shape of the opening 132 can be varied or a liquid crystal aperture portion can also be used. The aperture portion 130 itself may be replaced with any of apertures having the openings 132 in various shapes.

The image capturing unit 150 can receive the reflected light from the affected part P via the image forming unit 140 and the aperture portion 130 and capture an image of the affected part P.

More specifically, the image capturing unit 150 is disposed on the side opposite to the condenser lens 124 with respect to the light source 114 on the extension of the central axis of the cylindrical body 112. That is, the image capturing unit 150 is provided on the opposite side in the irradiation direction of the light source 114. The image capturing unit 150 has a camera cylindrical part 152, the imaging device 154 fixed in the camera cylindrical part 152, and an imaging lens 156 and a zoom mechanism 158 disposed in front of an image pickup face 154a of the imaging device 154.

The imaging device 154 has a CCD (Charge Coupled Device) and the like. The imaging lens 156 has an optical characteristic of forming an image of the image pickup face 154a of the imaging device 154 using the light from the affected part P. The zoom mechanism 158 has a zoom lens movable along the center axis of the camera cylindrical part 152 manually or by an actuator such as a motor. The zoom mechanism 158 has a role of enlarging/reducing an image of the irradiated affected part P. Obviously, each of the imaging lens 156 and the zoom lens may be constructed by a plurality of lens groups. Simple magnification variations may be performed for adjusting the imaging device 154 to achieve focus by moving the imaging lens 156.

The reflected light from the affected part P in the predetermined irradiated range enters from the image forming unit 140 to the image pickup face 154a via the opening 132 in the aperture portion 130, the hole 126 in the condenser lens 124, an approximate center portion of the light emitting elements 114a disposed in an annular shape and, further, the zoom mechanism 158 and the imaging lens 156.

The positions of the image forming unit 140 and the aperture portion 130 can be moved along the central axis of the cylindrical body 112. Preferably, the distance from the image forming unit 140 to the affected part P is set to 400 to 900 mm to sufficiently assure a work space for the operator to e.g. treat the affected part P.

Optical Characteristics of Apparatus

The optical characteristics of the apparatus will now be described referring to the optical path shown in FIG. 10. In FIG. 10, an optical path L1 is of light applied to an affected part, and an optical path L2 is of reflected light from the affected part.

First, light emitted from each of the light emitting elements 114a provided at one end of the cylindrical body 112 is converted to approximately parallel rays by the collimate lens 122. In this case, eight light emitting elements 114a are provided in an annular shape, so that approximately parallel rays shaped in an approximately cylindrical peripheral face are emitted.

The approximately parallel rays from the light emitting elements 114a are condensed to a predetermined position by the condenser lens 124. That is, in the medical imaging apparatus 110 according to the present embodiment, to condense light from the light emitting elements 114a as a plurality of light sources to a predetermined position, approximately parallel rays are once generated by each of the collimate lenses 122. The parallel rays are condensed to a common focal point by the single condenser lens 124. Consequently, light from the light emitting elements 114a as a plurality of light sources can be efficiently condensed. Between the condenser lens 124 and the aperture portion 130 in FIG. 10, the range of light entering the opening 132 in the aperture portion 130 out of the light outputted from the condenser lens 124 is shown with a linear line R.

The light condensed by the condenser lens 124 is then blocked except for the light passing through the opening 132 in the aperture portion 130. Desirably, the aperture portion 130 is positioned near a beam waist of the condenser lens 124 for the reason that the light of the light source having the plurality of light emitting elements 114a is efficiently controlled and the light is made uniform by reducing the influence of ununiformity.

The opening 132 in the aperture portion 130 has an approximately rectangular shape as described above, and the light passed through the aperture portion 130 is applied to the affected part P via the image forming unit 140. That is, in the present embodiment, it can be regarded that an image of light having an approximately rectangular shape formed by the aperture portion 130 falls on the affected part P by the image forming unit 140.

When the light is reflected by the affected part P irradiated in an approximately rectangular shape, the reflected light generally passes through, as diffuse reflection, the image forming unit 140 and an image is formed again near the opening 132 of the aperture portion 130. The imaged light passes through the hole 126 in the condenser lens 124 and enters the image capturing unit 150. The reflected light is incident on the image pickup face 154a of the imaging device 154 via the zoom mechanism 158 and the imaging lens 156 in the image capturing unit 150. In such a manner, an image of the affected part P is captured by the imaging device 154.

In the case of using the present medical imaging apparatus for dental application, the size, the optical characteristics, the position, and the like of each of the elements are set so that the range of the affected part P to be illuminated becomes about e.g. 80 mm×150 mm and the distance from the imaging lens 140 to the affected part P becomes about 400 to 900 mm.

In the medical imaging apparatus 110 constructed as described above, light emitted from the light source 114 is condensed by the light condenser 120, the condensed light is limited by the opening 132 in the aperture portion 130, and an image is formed on the affected part P via the image forming unit 140. Consequently, proper illuminance which is relatively high and is adapted to treatment or the like also on the affected part P remote from the light source 114 can be obtained. Since the image capturing unit 150 for receiving reflected light from the affected part P via the image forming unit 140 and the opening 132 in the aperture portion 130 and capturing an image of the affected part P is provided, the irradiation range and the image capture range can be made coincide with each other.

Moreover, the light emitted from the light source 114 is applied to the affected part P via the image forming unit 140, and reflected light from the affected part P also enters the image capturing unit 150 via the image forming unit 140. Consequently, since light passing near the optical axis of the image forming unit 140 is used as the reflected light, aberration and the like is relatively small, and an excellent image can be obtained.

In addition, the hole 126 is formed in an approximate center portion of the condenser lens 124, and the image capturing unit 150 receives reflected light from the affected part P via the hole 126. While eliminating the influence of the condenser lens 124 at the time of imaging, the irradiation range of the light source 114 and the image capture range can be made coincide with each other.

The affected part P can be brightly illuminated by the light emitting elements 114a disposed annularly. At the same time, a space for disposing the image capturing unit 150 can be provided in an approximate center portion.

Since LEDs are used as the light emitting elements 114a, heat generation amount in the light source 114 can be reduced.

Further, the zoom mechanism 158 is incorporated in the image capturing unit 150, so that the image capture range can be reduced/enlarged while maintaining the center of the illumination range constant.

Fourth Embodiment

Figure 12:
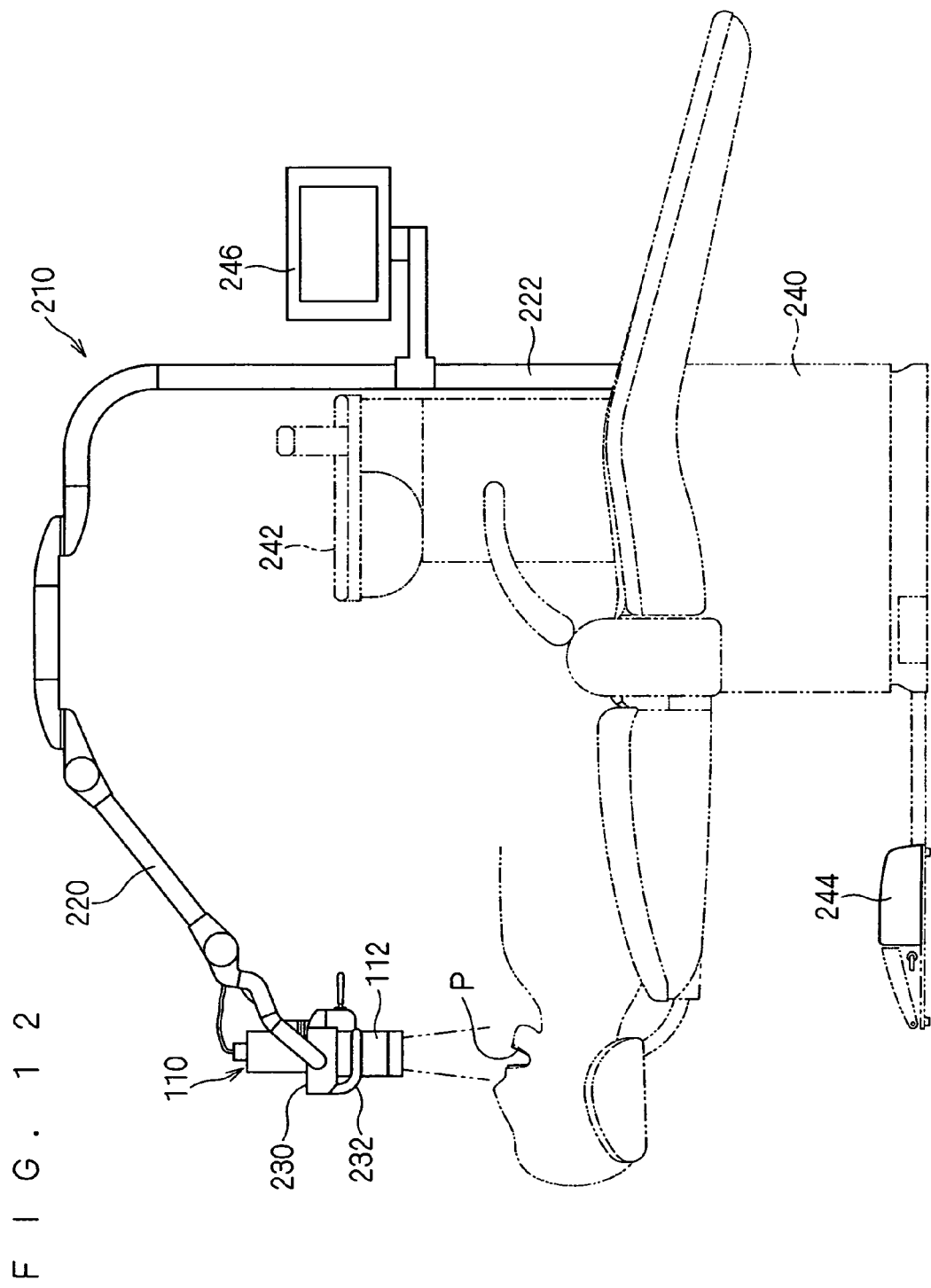
FIG. 12 is a schematic side view showing a general configuration of a medical imaging apparatus according to a fourth embodiment.
Figure 13:
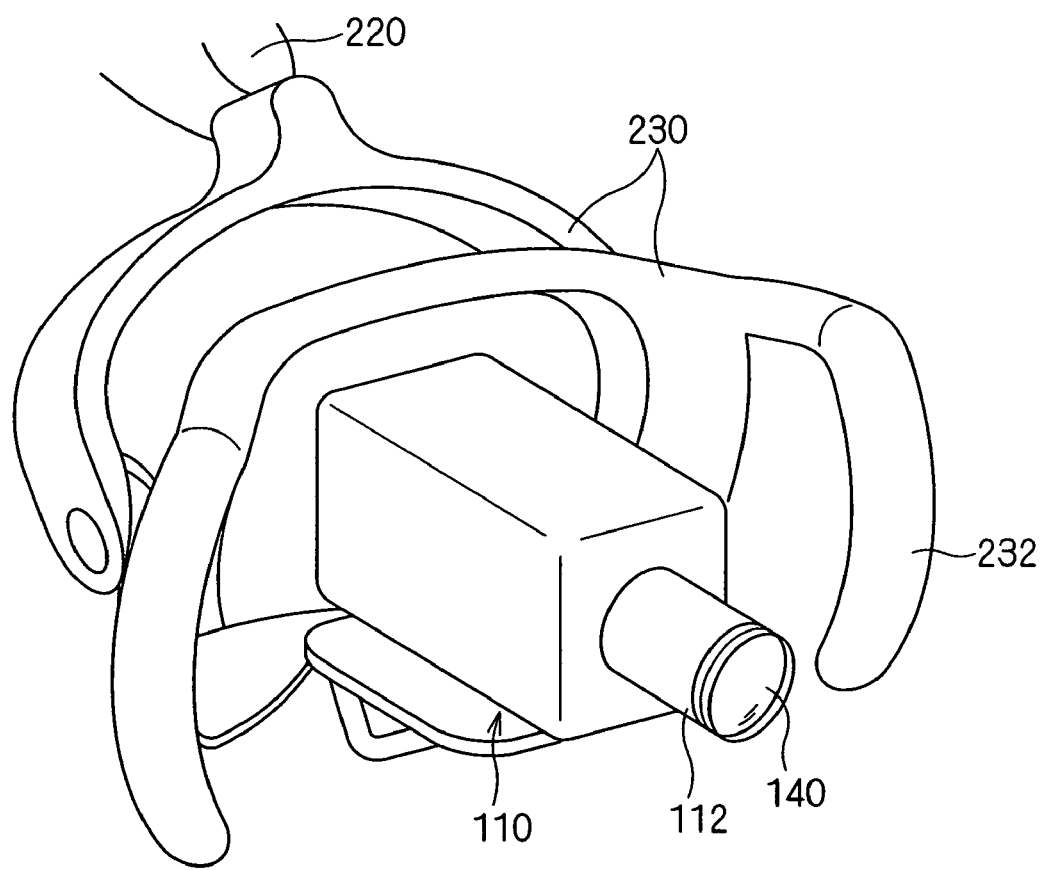
FIG. 13 is a schematic perspective view showing a main part of the medical imaging apparatus.
Figure 14:
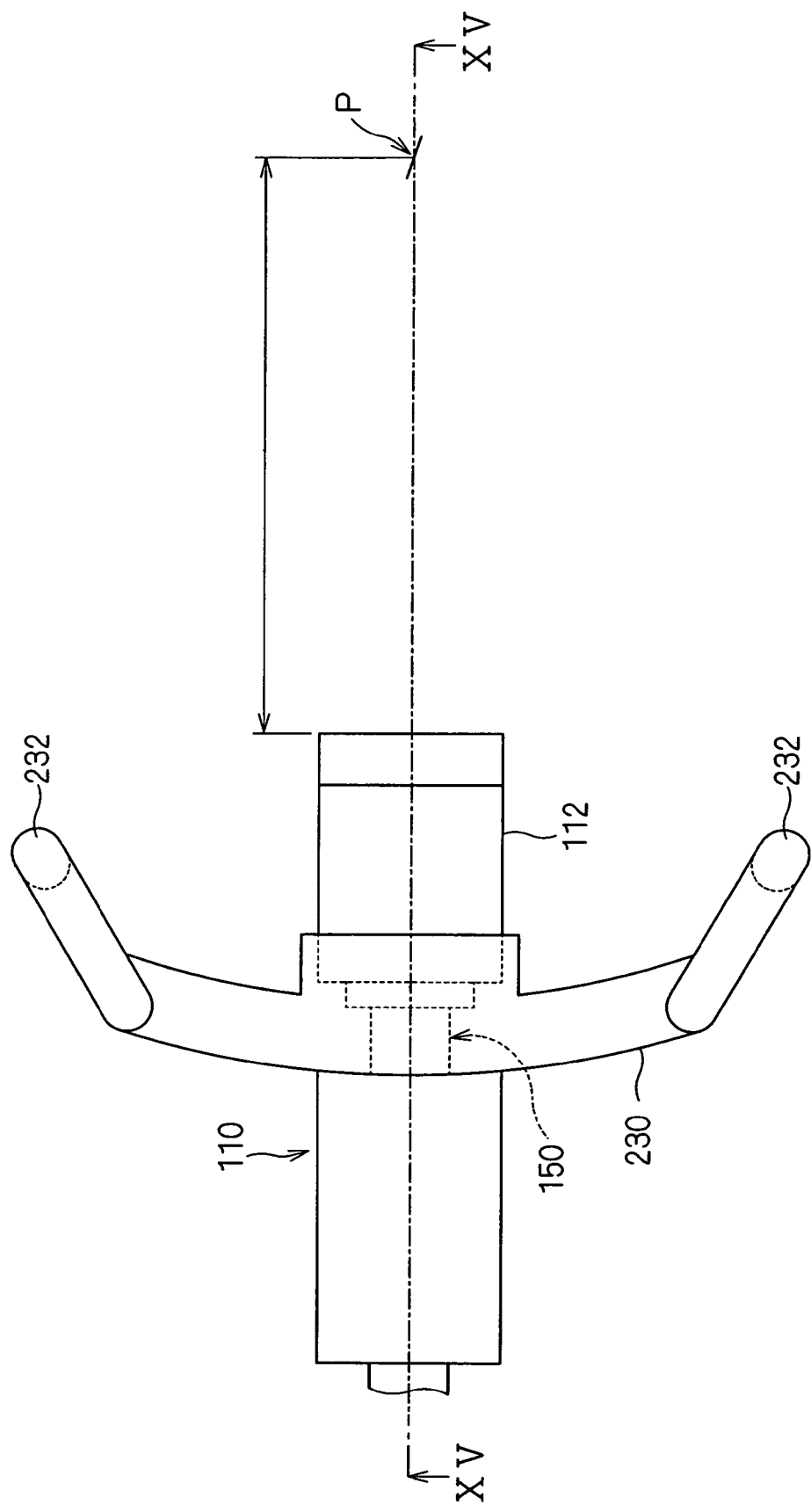
FIG. 14 is a schematic plan view showing a main part of the medical imaging apparatus.
Figure 15:
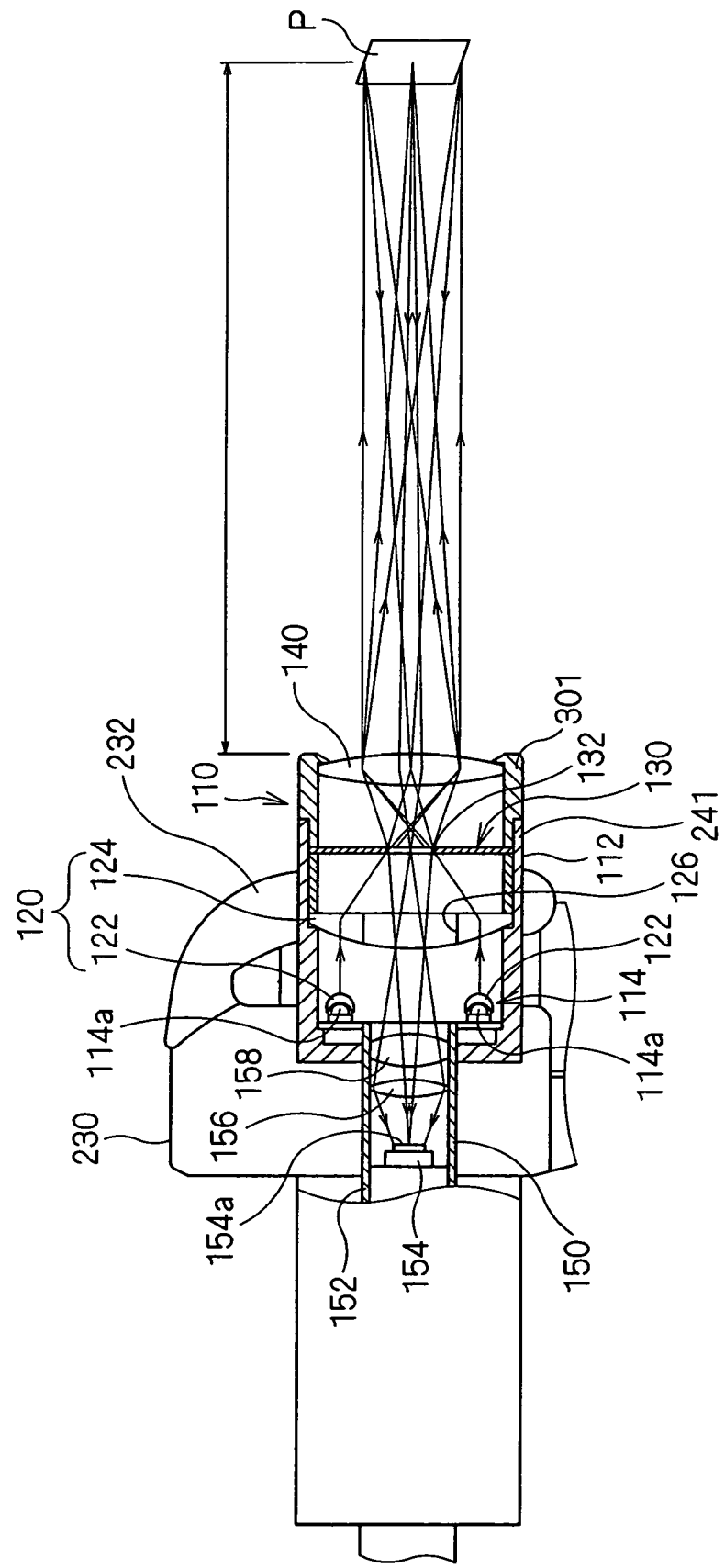
FIG. 15 is a cross sectional view taken along line XV-XV of FIG. 14.

A medical imaging apparatus according to a fourth embodiment will be described hereinbelow. FIG. 12 is a schematic side view showing a general configuration of the medical imaging apparatus. FIG. 13 is a schematic perspective view showing a main part of the medical imaging apparatus. FIG. 14 is a schematic plan view showing a main part of the medical imaging apparatus. FIG. 15 is a cross sectional view taken along line XV-XV of FIG. 14.

A medical imaging apparatus 210 has the components of the medical imaging apparatus 110 described in the third embodiment, and in addition thereto, a movable arm 220, and a frame 230 for fixing a configuration including the light source 114, the light condenser 120, the image forming unit 140, and the aperture portion 130 to the tip of the movable arm 220. The medical imaging apparatus 110 itself is similar to that of the third embodiment, so that the description of the configuration will not be repeated.

The movable arm 220 is attached to the upper end of a support 222 provided upright in a predetermined position. With a structure including a known link mechanism, the movable arm 220 can be maintained in a movably-bent predetermined posture.

The frame 230 is attached to the tip of the movable arm 220 and holds the medical imaging apparatus 110 in the third embodiment. The frame 230 is provided with a handle 232 so that the operator can easily move it.

The medical imaging apparatus 210 has, in addition to the above, a dental treatment chair 240, a spittoon 242 for gargle, a foot controller 244, and a display device 246.

The dental treatment chair 240 can support a patient so that the posture can be freely changed and the patient can be moved in the vertical direction in accordance with an operation on the foot controller 244. The spittoon 242 for gargle and the support 222 are provided adjacent to the dental treatment chair 240. The display device 246 is a liquid crystal display, a CRT (Cathode Ray Tube) display, or the like. The display device 246 is attached in some midpoint of the support 222 and displays an image captured by the medical imaging apparatus 110.

In such a medical imaging apparatus 210, the configuration including the light source 114, the light condenser 120, the image forming unit 140, and the aperture portion 130 can be movably supported. Therefore, the operator can perform a treatment work while disposing the medical imaging apparatus 110 in a predetermined posture and a predetermined position without supporting it by his/her hand.

Modification

In the case of using LEDs as the light emitting elements 114a as an application example of the medical imaging apparatus according to the embodiments, an LED of white color and an LED having a wavelength of 400±20 nm may be incorporated and turned on while being switched. It is known that when the oral cavity is irradiated with light having a wavelength of 400±20 nm in a dental diagnosis, a part where dental calculi or dental plaque is attached emits red fluorescence. It is also known that when the oral cavity is irradiated with light having a wavelength of 400±20 nm, an image useful for diagnosing a carious part can be also obtained, so that detection of a lesion part is facilitated. Consequently, by further incorporating the LED having a wavelength of 400±20 nm, in addition to the function capturing an image of an affected part P while illuminating the affected part P, dental diagnosis can be performed using an image captured while irradiating the affected part P with the light having a wavelength of 400±20 nm.

In the case of using LEDs as the light emitting elements 114a as another application example of the medical imaging apparatus according to the embodiments, an LED of white color and an LED having a wavelength of 470±20 nm may be incorporated and turned on while being switched. In the dental treatment, light having a wavelength of 470±20 nm is used for photopolymerizing the resin of the affected part P. Consequently, by further incorporating the LED having a wavelength of 470±20 nm, in addition to the function of capturing an image of an affected part P while illuminating the affected part P, dental treatment can be performed using an image captured while irradiating the affected part P with the light having a wavelength of 470±20 nm.

In the case of using LEDs as the light emitting elements 114a as another application example of the medical imaging apparatus according to any of the embodiments, an LED of white color and an LED having a wavelength of 405±20 nm may be incorporated and turned on while being switched or simultaneously turned on. In the dental field, light having a wavelength of 405±20 nm is used also for bleaching teeth. Consequently, by further incorporating the LED having a wavelength of 405±20 nm, in addition to the function of capturing an image of an affected part P while illuminating the affected part P, teeth can be bleached with the light having a wavelength of 405±20 nm.

The foregoing embodiments have been described by way of examples using the apparatus for irradiating the oral cavity (affected part) P of a patient in dental treatment. The apparatus is not limited in dental application but can also be used for imaging while irradiating an affected part such as an ear, nose, or the like in another medical field such as otolaryngology.

The configurations described in the foregoing embodiments and the modifications can be appropriately combined as long as they do not contradict each other.

While the invention has been shown and described in detail, the foregoing description is in all aspects illustrative and not restrictive. It is therefore understood that numerous modifications and variations can be devised without departing from the scope of the invention.

What is claimed is:

1. A medical imaging apparatus for irradiating an affected part with light and capturing an image of the affected part, comprising:
   a light source;
   a light condenser for condensing light emitted from said light source;
   an image forming unit for forming an image on said affected part from the light condensed by said light condenser;
   an aperture portion provided between said light condenser and said image forming unit and regulating passage of the light condensed by said light condenser; and
   an image capturing unit including an imaging device for receiving reflected light from said affected part via said image forming unit and said aperture portion and capturing an image of said affected part.

2. The medical imaging apparatus according to claim 1, further comprising:
a movable arm; and
a frame for fixing said light source, said light condenser, said image forming unit, and said aperture portion to a tip of said movable arm.

3. The medical imaging apparatus according to claim 1, wherein said light source has, as a light emitting element, one of a light emitting diode, a halogen lamp, a krypton lamp, and a semiconductor laser.

4. The medical imaging apparatus according to claim 1, wherein
said light source has a plurality of light emitting elements, said light condenser includes:
collimate lenses each provided on a light emission face of each of said light emitting elements; and
a condenser lens formed in an approximately annular shape with a hole in an approximate center portion, and for condensing light from said collimate lenses, and
said image capturing unit receives reflected light from said affected part via said hole in said condenser lens.

5. The medical imaging apparatus according to claim 4, wherein said plurality of light emitting elements are disposed in an approximately annular shape.

6. The medical imaging apparatus according to claim 4, wherein said light emitting element is a light emitting diode.

7. The medical imaging apparatus according to claim 1, wherein said aperture portion is disposed near a beam waist of said light condenser.

8. The medical imaging apparatus according to claim 1, wherein said aperture portion has an approximately rectangular-shaped opening.

9. The medical imaging apparatus according to claim 1, wherein said image capturing unit is disposed on a central axis of said light condenser and said image forming unit and has a zoom mechanism.

* * * * *